(12) United States Patent
Sones et al.

(10) Patent No.: US 7,379,177 B1
(45) Date of Patent: May 27, 2008

(54) SYSTEM AND METHOD FOR PERFORMING HARD GLASS INSPECTION

(75) Inventors: Richard A. Sones, Cleveland, OH (US); Amir Novini, Akron, OH (US)

(73) Assignee: Applied Vision Company, LLC, Cuyahoga Falls, OH (US)

( * ) Notice: Subject to any disclaimer, the term of this patent is extended or adjusted under 35 U.S.C. 154(b) by 115 days.

(21) Appl. No.: 11/382,300

(22) Filed: May 9, 2006

Related U.S. Application Data

(60) Provisional application No. 60/705,383, filed on Aug. 4, 2005.

(51) Int. Cl.
*G01N 21/00* (2006.01)

(52) U.S. Cl. ............................... 356/239.1; 356/237.2; 356/429; 356/240

(58) Field of Classification Search ............ 356/239.1, 356/237.2–237.5, 240, 429–431
See application file for complete search history.

(56) References Cited

U.S. PATENT DOCUMENTS

| | | | |
|---|---|---|---|
| 2,309,290 A | 1/1943 | Aksomitas | |
| 6,914,678 B1 * | 7/2005 | Ulrichsen et al. | 356/429 |
| 6,989,857 B2 * | 1/2006 | Furnas | 356/239.4 |
| 2001/0054680 A1 * | 12/2001 | Lindner | 250/223 B |
| 2005/0166413 A1 * | 8/2005 | Crampton | 33/503 |

* cited by examiner

*Primary Examiner*—L. G. Lauchman
*Assistant Examiner*—Iyabo S Alli
(74) *Attorney, Agent, or Firm*—Hahn Loeser & Parks; David J. Muzilla

(57) ABSTRACT

A system and method to inspect objects for a characteristic parameter. The system includes at least one electromagnetic source for emitting at least two separate wavelengths of electromagnetic energy. At least one electromagnetic detector is positioned at a predefined distance from the electromagnetic source to measure an incident intensity value of the electromagnetic energy at the two wavelengths. An object, placed between the electromagnetic source and the electromagnetic detector is irradiated with electromagnetic energy at the two wavelengths and the electromagnetic energy transmitted through the object is measured by the electromagnetic detector. The system includes a computer-based platform operationally connected to the electromagnetic detector for receiving intensity data values from the electromagnetic detector and for computing attenuation ratio values. The attenuation ratio values are used to determine a level of the characteristic parameter.

21 Claims, 4 Drawing Sheets

US 7,379,177 B1

SYSTEM AND METHOD FOR PERFORMING HARD GLASS INSPECTION

CROSS-REFERENCE TO RELATED APPLICATIONS/INCORPORATION BY REFERENCE

This U.S. patent application claims priority to and the benefit of Provisional U.S. Patent Application Ser. No. 60/705,383 filed on Aug. 4, 2005.

TECHNICAL FIELD

Certain embodiments of the present invention relate to inspection systems. More particularly, certain embodiments of the present invention relate to a system and method for inspecting glass objects for a desired characteristic parameter such as, for example, "hardness" on a processing line in order to detect and eliminate any objects on the processing line that do not embody the desired characteristic parameter and/or to monitor the process to ensure the characteristic parameter is not deviating from a specified allowable range.

BACKGROUND OF THE INVENTION

During a production process, objects such as glass bottles typically go through an annealing oven to take all of the internal stresses out of the bottles. Glass, for example, is made soft by heating and then slow cooling to eliminate internal stresses. Such objects are still somewhat fragile and can break or crack rather easily when subjected to a rather moderate external force.

On the other hand, during a production process, objects such as glass car windows may go through a tempering process to deliberately set up stresses in the window. Such a tempering process allows the window to better resist impact forces to help prevent the window from failing. Even when the impact forces are large enough to damage the window, the window fails in a safer, more graceful manner. For example, the window may crack but will not shatter and spread glass shards all around.

Tempering and annealing are two opposite extremes that can be achieved when producing, for example, glass or glass-based objects. However, it is often desirable to produce an object having a certain characteristic parameter (e.g., a "hard" object" or a "hardened" object) which is between the annealed state and the tempered state to make it stronger. Glass bottles, for example, may be hardened by cooling the bottles in a particular manner when they come out of the mold as described in, for example, U.S. Pat. No. 2,309,290 to Aksomitas entitled "Cooling Nozzle for Tempering Hollow Glassware".

The benefits of such hardened objects are clear for the glass container industry. First of all, the consumer will not be able to accidentally break a hardened glass container as easily. In addition, today, the speed of glass container processing lines (e.g., a bottle filling processing line) are often limited by how easily the glass object will break.

For example, if glass bottles are traveling down a filling line and a bottle gets jammed, then a next bottle coming down the line may crash into the jammed bottle causing one or both bottles to shatter if the next bottle is traveling too fast. Therefore, the speed of such processing lines are deliberately limited today in order to avoid such catastrophic crashes. However, if the glass bottles can be hardened, the speed of the processing line could be significantly increased, generating improved processing efficiencies.

However, when producing many glass objects, such as glass bottles or jars, using a particular hardening process, it is often difficult to determine if any particular glass object has been properly hardened, or if the hardening process is deviating from a specified range. For example, if a glass bottle is hardened improperly such that unbalanced stresses are set up within the bottle, then a very minimal external force experienced by the bottle may cause the bottle to catastrophically fail (e.g., shatter or explode). Similarly, if a glass bottle is not properly hardened, the bottle may end up being too soft and, therefore, not much better than an un-hardened bottle.

Therefore there remains a need in the art for a fast and convenient way to efficiently determine a characteristic parameter (e.g., "a hardness") of an object (e.g., a glass bottle), particularly as the object travels along an automated processing line (e.g., a bottle manufacturing line) with other similar objects.

Further limitations and disadvantages of conventional, traditional, and proposed approaches will become apparent to one of skill in the art, through comparison of such systems and methods with the present invention as set forth in the remainder of the present application with reference to the drawings.

BRIEF SUMMARY OF THE INVENTION

An embodiment of the present invention comprises a method to inspect an object for a characteristic parameter. The method comprises measuring an incident intensity level of electromagnetic energy of at least two wavelengths emitted from at least one electromagnetic source at a predefined distance from the at least one electromagnetic source using at least one electromagnetic detector positioned at the predefined distance from the at least one electromagnetic source. The method further comprises positioning the object in proximity to the at least one electromagnetic source such that the at least one electromagnetic source irradiates at least a portion of the object at the at least two wavelengths. The method also comprises measuring a transmitted intensity level of the electromagnetic energy, at the at least two wavelengths, through the object using the at least one electromagnetic detector. The method further comprises generating at least one attenuation ratio from the at least two measured incident intensity levels and the at least two measured transmitted intensity levels at the at least two wavelengths using a computer-based platform operationally connected to the electromagnetic detector. The method also comprises determining if the object includes the characteristic parameter based on the at least one attenuation ratio.

Another embodiment of the present invention comprises a system to inspect an object for a characteristic parameter. The system comprises at least one electromagnetic source emitting at least two separate wavelengths of electromagnetic energy. The system further includes an electromagnetic detector positioned at a predefined distance from the at least one electromagnetic source and measuring an incident intensity value of the electromagnetic energy at each of the at least two wavelengths at the predefined distance from the at least one electromagnetic source. The electromagnetic detector also measures a transmitted intensity value of the electromagnetic energy at each of the at least two wavelengths through an object positioned between the at least one electromagnetic source and the at least one electromagnetic detector. The system also comprises a computer-based platform operationally connected to the at least one electromagnetic detector to receive the incident intensity values and the transmitted intensity values and to generate at least one attenuation ratio in response to the intensity values. The computer-based platform also determines if the object includes the characteristic parameter based on the at least one attenuation ratio.

These and other advantages and novel features of the present invention, as well as details of illustrated embodiments thereof, will be more fully understood from the following description and drawings.

DETAILED DESCRIPTION OF THE INVENTION

Figure 1:
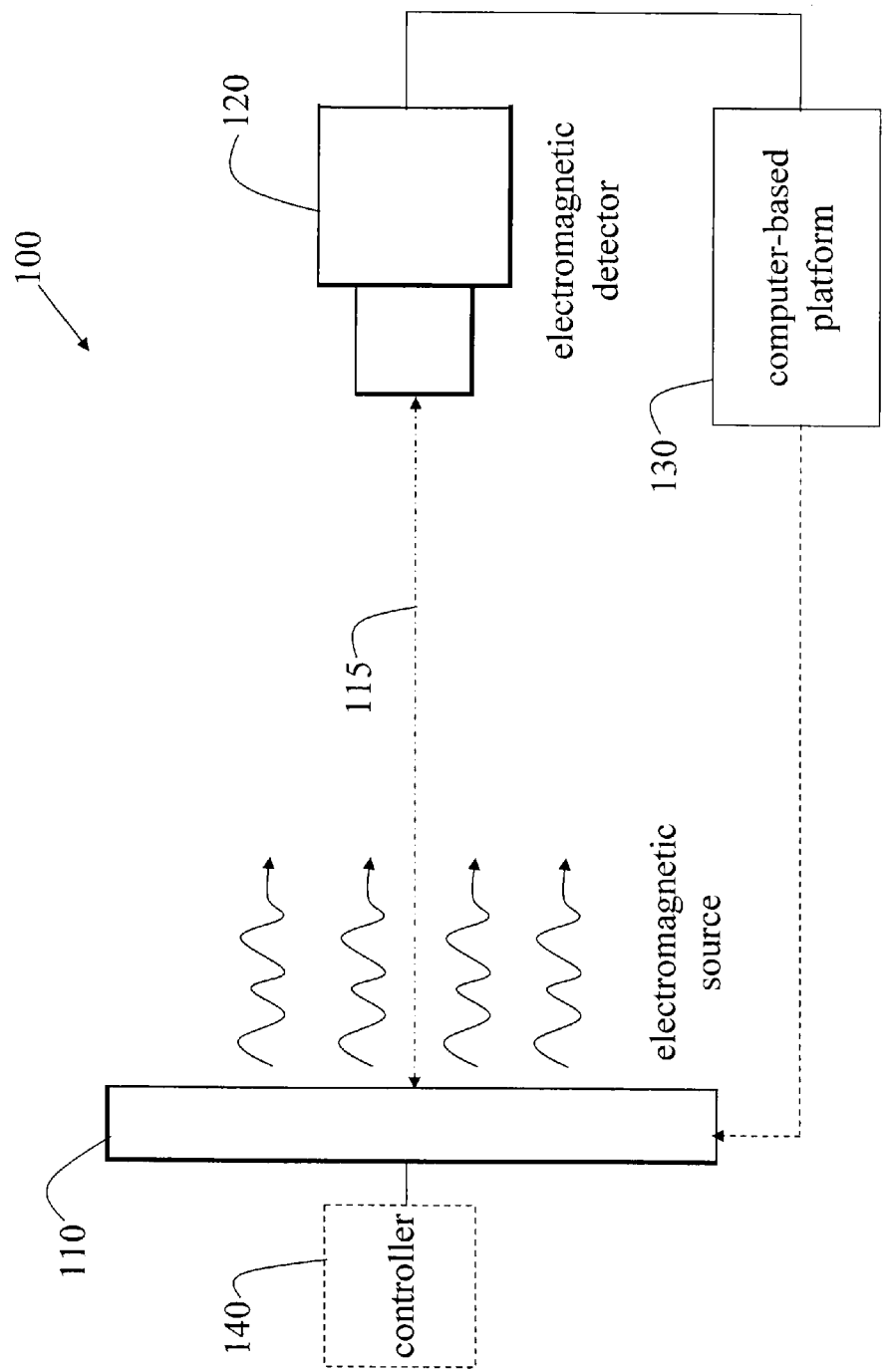
FIG. 1 is a schematic block diagram of an embodiment of a system to inspect an object for a characteristic parameter, in accordance with various aspects of the present invention.

FIG. 1 is a schematic block diagram of an embodiment of a system 100 to inspect an object for a characteristic parameter, in accordance with various aspects of the present invention. The system comprises at least one electromagnetic source 110, at least one electromagnetic detector 120, and a computer-based platform 130. The electromagnetic detector 120 is positioned at a predetermined distance 115 from the electromagnetic source 110. The electromagnetic detector 120 senses electromagnetic energy radiated by the electromagnetic source 110 and measures the sensed electromagnetic energy levels. The electromagnetic detector 120 operationally interfaces to the computer-based platform 130 such that the computer-based platform receives sensed electromagnetic energy level data from the electromagnetic detector 120.

In accordance with various embodiments of the present invention, the electromagnetic source 110 may comprise, for example, a source of visible light such as an array of red, green, and blue wavelength light-emitting diodes (LED's) or a source of white light. The electromagnetic source 110 may also comprise, for example, a source of X-rays, an infrared source, an ultraviolet source, or any other source of electromagnetic energy or combination thereof that may be deemed appropriate for certain applications of various embodiments of the present invention.

In accordance with various embodiments of the present invention, the electromagnetic detector 120 may comprise, for example, at least two monochromatic cameras each tuned to a different wavelength, a color camera, a charge-coupled device (CCD) camera, a photo-cell or photo-detector, an X-ray detector, an infrared energy detector, an ultra-violet energy detector, or any combination thereof. The electromagnetic detector 120 matches the electromagnetic source 110 in that the electromagnetic detector 120 is capable of detecting at least certain wavelengths of energy emitted by the electromagnetic source 110.

In accordance with various embodiments of the present invention, the computer-based platform 130 may comprise, for example, a personal computer (PC), a work station, a digital signal processor (DSP), an application specific integrated circuit (ASIC), a central processing unit (CPU), or any other computer-based unit having the processing capability to perform the various functions associated with embodiments of the present invention. For example, the computer-based platform 130 could be implemented all in hardware (e.g., as an ASIC), in accordance with an embodiment of the present invention, or may be implemented as a combination of software and hardware (e.g., a computer program running on a CPU in a PC), in accordance with another embodiment of the present invention.

As an option, the system 100 may further include a controller 140 which operationally interfaces to the electromagnetic source 110 to, for example, control the timing of when certain wavelength sources turn on and off. For example, if the electromagnetic source 110 comprises an array of red, green, and blue wavelength LED's, then the controller 140 may operationally turn the red, green, and blue LED's on and off in succession (e.g., first red, then green, then blue). The electromagnetic detector 120 detects the emitted red, green, and blue light in succession as well. As an alternative option, the computer-based platform 130 may operationally interface to the electromagnetic source 110 and provide the controlling functionality. As a result, a separate controller 140 would not be needed.

A monochrome camera may be used as the electromagnetic detector 120 if the red, green, and blue LED's are strobed in sequence. If all of the red, green, and blue LED's are turned on at the same time, then a color camera could be used as the electromagnetic detector 120 to measure the red, green, and blue wavelengths.

Each element of the system 100 requires a source of electrical power even though the source (or sources) of electrical power is (are) not shown in the figures.

Figure 2:
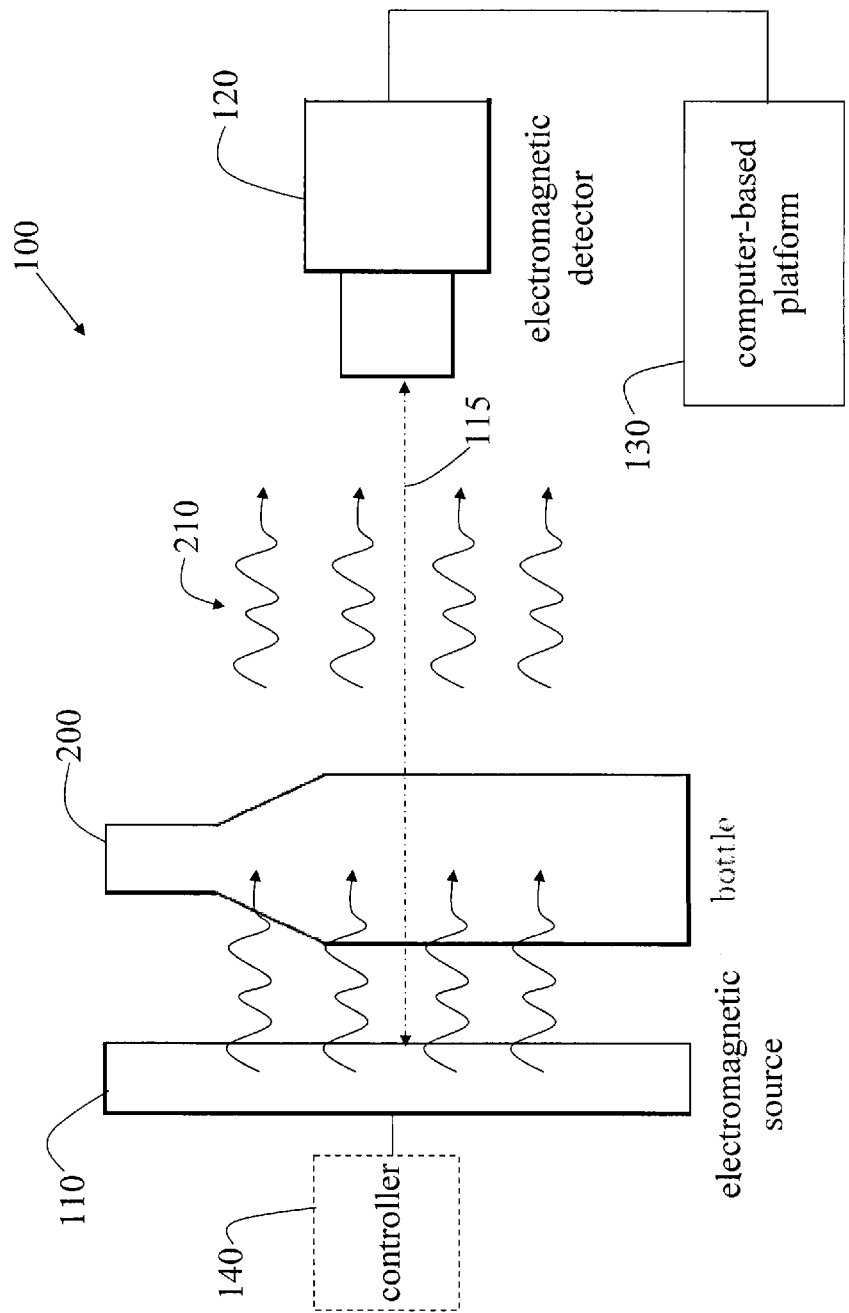
FIG. 2 is a schematic block diagram of the system of FIG. 1 illustrating how the system is used to inspect an object for a characteristic parameter, in accordance with an embodiment of the present invention.

FIG. 2 is a schematic block diagram of the system 100 of FIG. 1 illustrating how the system 100 is used to inspect an object 200 for a characteristic parameter. The object 200 (e.g., a glass bottle) is placed between the electromagnetic source 110 and the electromagnetic detector 120 such that at least a portion of the electromagnetic energy 210 which is emitted from the source 110 is transmitted through the object 200 and appears at the detector 120. The energy detected by the detector 120 is attenuated by the object 200. That is, the magnitude of the energy is reduced in intensity or amplitude by virtue of having passed through the object 200. The amount of attenuation is dependent on the object and the wavelength of the electromagnetic energy. By measuring the amount of attenuation that occurs through the object 200 at different wavelengths, a characteristic parameter (e.g., an attenuation ratio representing a hardness level) of the object 200 may be determined. The attenuation ratio may be used to determine if the hardness level is acceptable or not (e.g., by comparing the attenuation ratio to a desired value or range of values that represent an acceptable hardness level).

Figure 3:
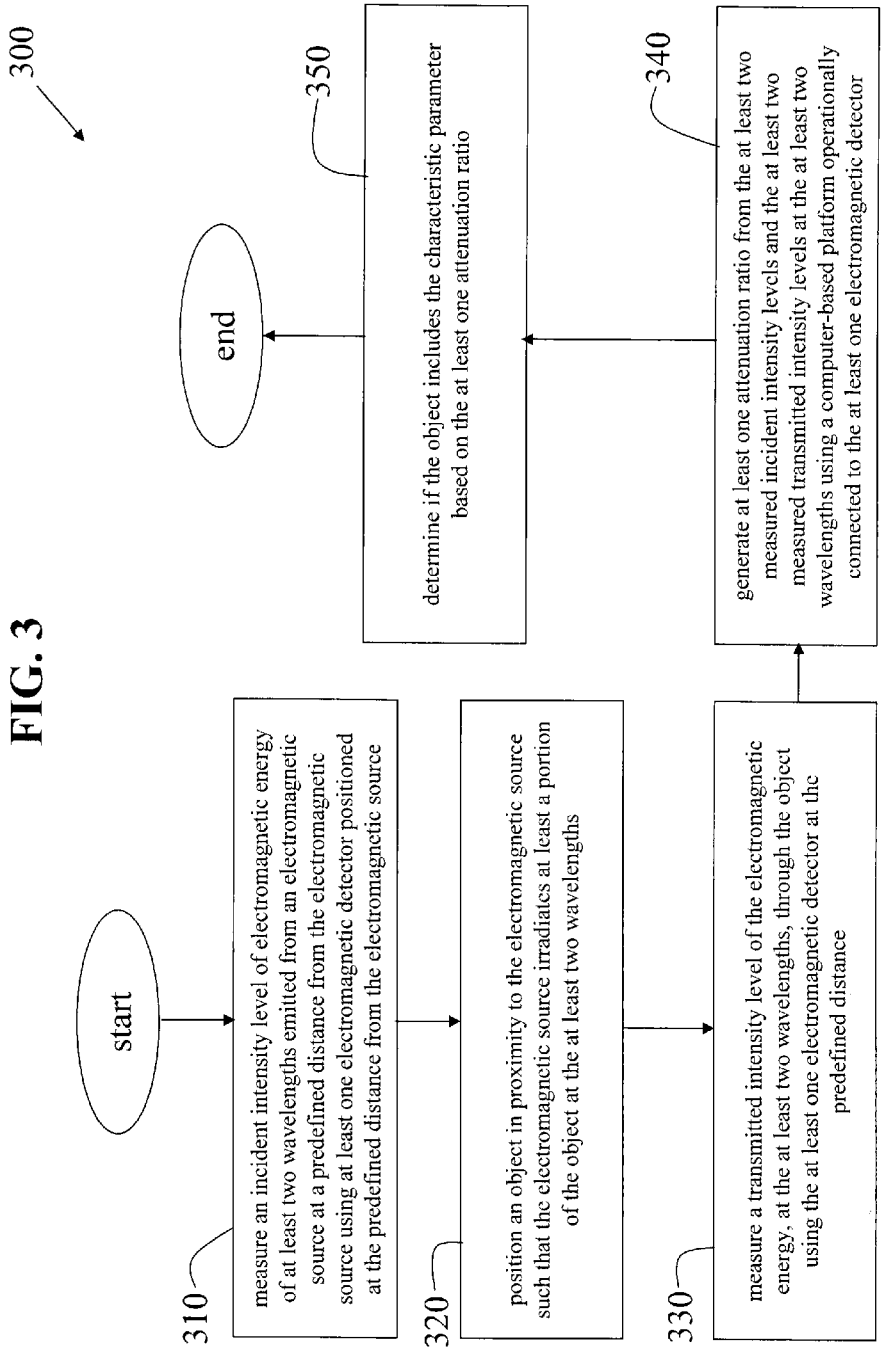
FIG. 3 illustrates a flowchart of an embodiment of a method to inspect an object for a characteristic parameter using the system of FIGS. 1-2, in accordance with various aspects of the present invention.

FIG. 3 illustrates a flowchart of an embodiment of a method 300 to inspect an object for a characteristic parameter using the system 100 of FIGS. 1-2, in accordance with various aspects of the present invention. In step 310, an incident intensity level of electromagnetic energy emitted from at least one electromagnetic source is measured at two wavelengths, at least, at a predefined distance from the electromagnetic source using at least one electromagnetic detector positioned at the predefined distance from the electromagnetic source. In step 320, an object is positioned in proximity to the electromagnetic source such that the electromagnetic source irradiates at least a portion of the object at the at least two wavelengths. In step 330, a transmitted intensity level of electromagnetic energy is measured, at the at least two wavelengths, through the object using the at least one electromagnetic detector at the predefined distance. In step 340, at least one attenuation ratio is generated from the at least two measured incident intensity levels and the at least two measured transmitted intensity levels at the at least two wavelengths using a computer-based platform operationally connected to the at least one electromagnetic detector. In step 350, the at least one attenuation ratio is used to determine if the object includes the characteristic parameter based on the at least one attenuation ratio (e.g., by comparing the attenuation ratio to at least one predetermined threshold value to decide if the object has the characteristic parameter using the computer-based platform).

In accordance with the theory on which embodiments of the present invention are based, the attenuation of a monochromatic beam of light passing through an absorptive (or weakly scattering) medium obeys the Beer-Lambert law:

$$I(\lambda) = I_o(\lambda) e^{-\alpha(\lambda) x},$$

where $I_o$ and $I$ are the incident and transmitted intensities, $\alpha$ is the attenuation coefficient of the medium, x is the thickness of the medium, and $\lambda$ is the wavelength of the light. The attenuation of the electromagnetic energy (e.g., light) is exponential through, for example, a glass bottle. If the incident and transmitted intensities are measured at two different wavelengths, $\lambda_1$ and $\lambda_2$, then the ratio of the attenuation coefficients at these two wavelengths is $$\alpha_1/\alpha_2 = [\ln(I_{o1}/I_1)]/[\ln(I_{o2}/I_2)]$$

where $$I_{oi} = I_o(\lambda_i)$$

$$I_i = I(\lambda_i)$$

$$\alpha_i \equiv \alpha(\lambda_i)$$

and i=1, 2.

The important feature of the ratio $\alpha_1/\alpha_2$ is that it is independent of x, the thickness of the medium. Therefore, even though the thickness of glass bottles of a certain type may vary from bottle to bottle (or even across a same bottle) the calculated attenuation ratio is independent of such thickness variations.

Experiments on glass objects such as hardened bottles have shown that, if the wavelengths of electromagnetic energy $\lambda_1$ and $\lambda_2$ are chosen carefully, then the resultant attenuation ratio $\alpha_1/\alpha_2$ correlates well with a hardness level of the glass. That is, glass bottles may be inspected using the system of FIGS. 1 and 2 and the method of FIG. 3 to determine if the glass bottles have been hardened correctly. The coloring of the glass bottles to be inspected will affect the results and the required brightness of the light source (i.e., intensity of the electromagnetic source 110) and which colors or wavelengths may practically be used. Each type of bottle or glass is calibrated. That is, the incident intensity, $I_o(\lambda)$, with no bottle present is measured at each color or wavelength.

As an alternative, more than one attenuation ratio may be calculated by measuring the incident and transmitted intensities for at least three wavelengths. For example, if the electromagnetic source 110 is an array of red, green, and blue LED's, then an attenuation coefficient may be calculated for each wavelength of light (i.e., $\alpha_{red}$, $\alpha_{green}$, $\alpha_{blue}$) and several attenuation ratios (e.g., $\alpha_{red}/\alpha_{green}$, $\alpha_{red}/\alpha_{blue}$, $\alpha_{green}/\alpha_{blue}$) may be formed. Using at least two or all three of the attenuation ratios may help to better discern a desired hardness level from an undesired hardness level. Various combinations of the attenuation ratios may also be used to discern other desired characteristic parameter levels from other undesired characteristic parameter levels or defects, as well.

In accordance with an embodiment of the present invention, the calculation of at least one attenuation ratio may be performed on a pixel-by-pixel basis. That is, the electromagnetic detector 120 and computer-based platform 130 may generate an image of pixels for the incident energy and the transmitted energy over a region-of-interest (ROI) of the object 200. Each pixel corresponds to a different line of electromagnetic transmission through the object. As a result, attenuation ratios may be formed for each pixel within the ROI. Therefore, for example, a determination of appropriate hardness level of a bottle may be performed for each pixel in the ROI. In accordance with an embodiment of the present invention, a predetermined percentage or number of the pixels may need to "pass" the hardness level test (e.g., by comparing the attenuation coefficient of each pixel to a predefined threshold value) in order to declare that the bottle is "good" (i.e., has been properly hardened).

Also, by having attenuation ratio information for each pixel in the ROI, gradients of hardness levels across various dimensions of the ROI (and, therefore, across the glass bottle) may be determined. Determination of such gradients may help to identify certain problems in the hardening process. Also, a distribution of the pixel attenuation ratios may be formed and statistical analyses may be performed to, for example, determine a uniformity of hardness across the glass bottle.

In accordance with an embodiment of the present invention, the system 100 is set up on a processing line where glass objects (e.g., bottles) are traveling down the processing line. The system 100 may inspect each bottle as the bottles pass between the electromagnetic source 110 and the electromagnetic detector 120. Any "bad" bottles (i.e., bottles that have been determined to have been improperly hardened) may be ejected from the processing line. Alternatively, the system 100 may periodically sample bottles (e.g., every 100 bottles) simply to determine if the hardening process is drifting out of control or not (i.e., the process is monitored).

Figure 4:
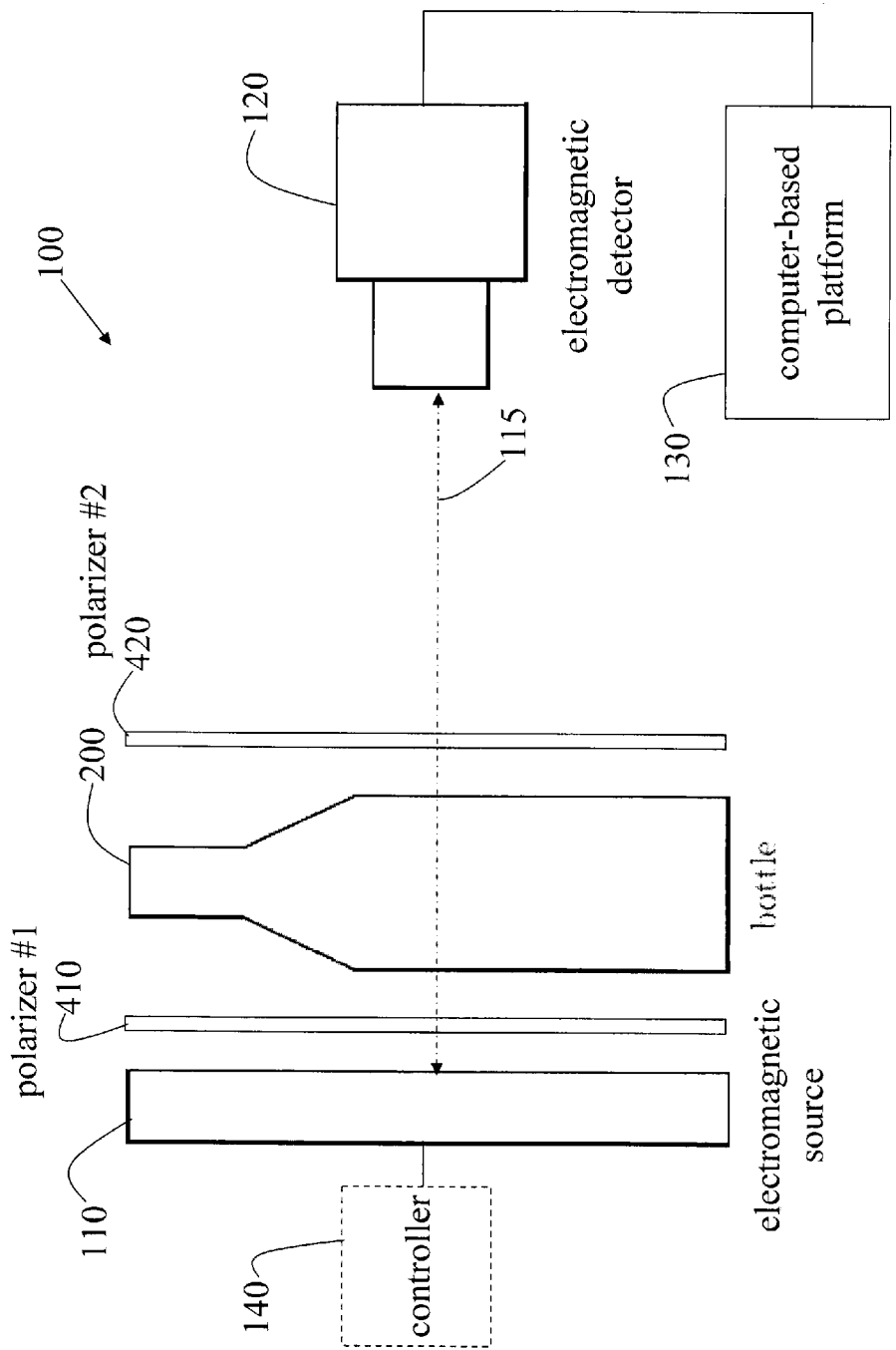
FIG. 4 is a schematic block diagram of an alternative embodiment of a system to inspect an object for a characteristic parameter, in accordance with various aspects of the present invention.

FIG. 4 is a schematic block diagram of an alternative embodiment of the system 100 to inspect an object for a characteristic parameter, in accordance with various aspects of the present invention. The system 100 of FIG. 4 adds two polarizers 410 and 420, where the first polarizer 410 is between the electromagnetic source 110 and the object 200 and the second polarizer 420 is between the object 200 and the electromagnetic detector 120. A polarizer is a device or material that transmits electromagnetic energy whose electric field vector is oriented in the same polarizing direction as that of the polarizer. The polarizer absorbs electromagnetic energy having electric field vectors at right angles to the polarizing direction of, for example, a linear polarizer.

The two polarizers 410 and 420 may be linear polarizers or circular polarizers and are configured such that the two polarizers together form a cross-polarized configuration. For example, if the polarizers 410 and 420 are linear polarizers, the two polarizers may be configured such that there axes of polarization are oriented at 90 degrees with respect to each other, thus forming a cross-polarized configuration. Other angles of relative orientation may be configured as well, in accordance with various embodiments of the present invention. If circular polarizers are used, the first polarizer 410 may be, for example, a left-hand circular polarizer and the second polarizer 420 may be a right-hand circular polarizer, thus forming a cross-polarized configuration. The cross-polarized configurations allow little or no electromagnetic energy to reach the electromagnetic detector 120 from the electromagnetic source 110 when no object 200 is present between the polarizers.

During operation, with an object 200 between the two polarizers, electromagnetic energy emitted from the electromagnetic source 110, and being of a certain first polarization, passes through the first polarizer 410 and then through the object 200 where the energy is attenuated. The energy that passes through the object 200 next experiences the second polarizer 420 which is of an opposite or crossed polarization to that of the first polarizer 410. Normally, this second polarizer 420 would allow little or no light or electromagnetic energy to pass since the energy transmitted through the object 200 is already of a significantly different polarization than the polarization of the second polarizer. However, if certain stresses due to hardening have been set up in the object 200, some of the electromagnetic energy will likely get through the second polarizer 420 to the electromagnetic detector 120 due to secondary polarization effects induced by the object 200. The electromagnetic energy that gets to the detector 120 may allow an image to be formed which resembles patterns of rings or loops on a topographic map, for example, representing the stress patterns in the object 200.

As a result, certain cross-polarized orientations of the polarizers 410 and 420 may allow for larger differences in attenuation ratios to be observed between properly hardened objects and improperly hardened objects (e.g., glass bottles). That is, better discrimination between properly and improperly hardened objects may be achieved.

In summary, a system and method to inspect an object for a characteristic parameter are disclosed. At least one electromagnetic source is calibrated with at least one electromagnetic detector for at least two wavelengths. The electromagnetic source irradiates an object placed between the source and the detector and measurements of electromagnetic intensity are made by the detector. A computer-based platform is used to generate attenuation ratios using the measured intensities and resultant calibration intensities. The attenuation ratios are used to determine a level of a characteristic parameter of the object.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method to inspect glass object for a hardness characteristic parameter, said method comprising:

measuring an incident intensity level of electromagnetic energy of at least two wavelengths emitted from at least one electromagnetic source at a predefined distance from said at least one electromagnetic source using at least one electromagnetic detector positioned at said predefined distance from said at least one electromagnetic source;

positioning said glass object in proximity to said at least one electromagnetic source such that said at least one electromagnetic source irradiates at least a portion of said glass object at said at least two wavelengths;

measuring a transmitted intensity level of said electromagnetic energy, at said at least two wavelengths, through said glass object using said at least one electromagnetic detector at said predefined distance;

generating at least one attenuation ratio from said at least two measured incident intensity levels and said at least two measured transmitted intensity levels at said at least two wavelengths using a computer-based platform operationally connected to said at least one electromagnetic detector; and determining if said glass object has an acceptable hardness characteristic parameter based on said at least one attenuation ratio.

2. The method of claim 1 wherein said determining is accomplished by comparing said at least one attenuation ratio to at least one predetermined hardness-related threshold value using said computer-based platform.

3. The method of claim 1 wherein said at least two wavelengths of electromagnetic energy are selected from the group consisting of visible light, infrared energy, ultraviolet energy, and X-ray energy.

4. The method of claim 1 wherein said method is implemented on a processing line to inspect a plurality of said glass objects, one after another, for said hardness characteristic parameter.

5. The method of claim 4 further comprising ejecting said glass object from said processing line when said glass object is determined to have an unacceptable hardness characteristic parameter.

6. The method of claim 1 wherein said method is periodically implemented on a processing line to inspect a subset of a plurality of said glass objects in order to monitor a hardness characteristic parameter process.

7. The method of claim 1 wherein said method is performed simultaneously for each of a plurality of pixels formed by said at least one electromagnetic detector, where each of said plurality of pixels corresponds to a different line of transmission through said object within a region-of-interest of said object.

8. The method of claim 7 further comprising determining a percentage of said plurality of pixels that have an acceptable hardness characteristic parameter.

9. The method of claim 8 further comprising comparing said percentage to a percentage threshold value to determine if said hardness characteristic parameter of said glass object is acceptable or unacceptable.

10. The method of claim 7 further comprising performing a gradient analysis on a plurality of attenuation ratios determined for said plurality of pixels.

11. The method of claim 7 further comprising performing a statistical analysis on a plurality of attenuation ratios determined for said plurality of pixels.

12. A system to inspect glass object for a characteristic hardness, said system comprising:

at least one electromagnetic source emitting at least two separate wavelengths of electromagnetic energy;

at least one electromagnetic detector positioned at a predefined distance from said at least one electromagnetic source for measuring an incident intensity value of said electromagnetic energy at each of said at least two wavelengths at said predefined distance from said at least one electromagnetic source, and for measuring a transmitted intensity value of said electromagnetic energy at each of said at least two wavelengths through an glass object positioned between said at least one electromagnetic source and said at least one electromagnetic detector; and a computer-based platform operationally connected to said at least one electromagnetic detector to receive said incident intensity values and said transmitted intensity values and to generate at least one attenuation ratio in response to said intensity values and to determine if said glass object has an acceptable characteristic hardness based on said at least one attenuation ratio.

13. The system of claim 12 wherein said computer-based platform determines if said glass object includes said acceptable characteristic hardness by comparing said at least one attenuation ratio to at least one predetermined threshold value.

14. The system of claim 12 wherein said system is part of a processing line for processing a plurality of said objects.

15. The system of claim 12 wherein said at least one electromagnetic detector is selected from the group consisting of at least one monochromatic camera, a color camera, a CCD camera, at least one photocell, an X-ray detector, an infrared energy detector, and an ultraviolet energy detector.

16. The system of claim 12 wherein said at least one computer-based platform is selected from the group consisting of a personal computer (PC), a workstation, a digital signal processor (DSP), an application specific integrated circuit (ASIC), and a central processing unit (CPU).

17. The system of claim 12 wherein said at least one electromagnetic source is selected from the group consisting of a visible light source, an infrared source, an ultraviolet source, and an X-ray source.

18. The system of claim 12 further comprising a controller operationally connected to said at least one electromagnetic source for controlling said electromagnetic source.

19. The system of claim 12 further comprising:

a first polarizer positioned between said at least one electromagnetic source and said object; and a second polarizer positioned between said object and said at least one electromagnetic detector.

20. The system of claim 12 wherein said computer-based platform is further operationally connected to said at least one electromagnetic source to control said at least one electromagnetic source.

21. A method to inspect a glass object, said method comprising irradiating said glass object with at least two electromagnetic wavelengths to determine at least one hardness characteristic of said glass object in response to at least one attenuation ratio derived, at least in part, from measurements of said at least two electromagnetic wavelengths through said glass object.

* * * * *